United States Patent [19]
Miller

[11] Patent Number: 5,235,974
[45] Date of Patent: Aug. 17, 1993

[54] HEATED BRA ARRANGEMENT

[76] Inventor: Darlene M. Miller, 4016 Maple Dr., Chesapeake, Va. 23321

[21] Appl. No.: 894,869

[22] Filed: Jun. 8, 1992

[51] Int. Cl.$^5$ ............................................. A61F 7/00
[52] U.S. Cl. ..................... 607/108; 604/291; 450/38
[58] Field of Search ................. 128/399–403, 128/379, 380, 382; 62/530; 604/291; 450/1, 38, 55, 69; 2/65

[56] References Cited

U.S. PATENT DOCUMENTS

| | | | |
|---|---|---|---|
| 2,298,361 | 10/1942 | Freund | 128/402 |
| 3,392,264 | 7/1968 | Arron | 128/382 |
| 3,500,832 | 3/1970 | Nunnery | 128/402 |
| 5,050,595 | 9/1991 | Krafft | 128/379 |

FOREIGN PATENT DOCUMENTS

| 2285902 | 4/1976 | France | 128/380 |
|---|---|---|---|

Primary Examiner—Mark S. Graham
Attorney, Agent, or Firm—Leon Gilden

[57] ABSTRACT

A heated bra is arranged to relieve engorgement in a lactating mother, wherein the bra structure includes a heated wire member directed coextensively in surrounding relationship relative to each cup member in electrical communication with an electrical energy source. The bra structure is further arranged to include a fluid impermeable chamber to accommodate heated water and other fluids to assist in relieving pressure to an individual.

1 Claim, 4 Drawing Sheets

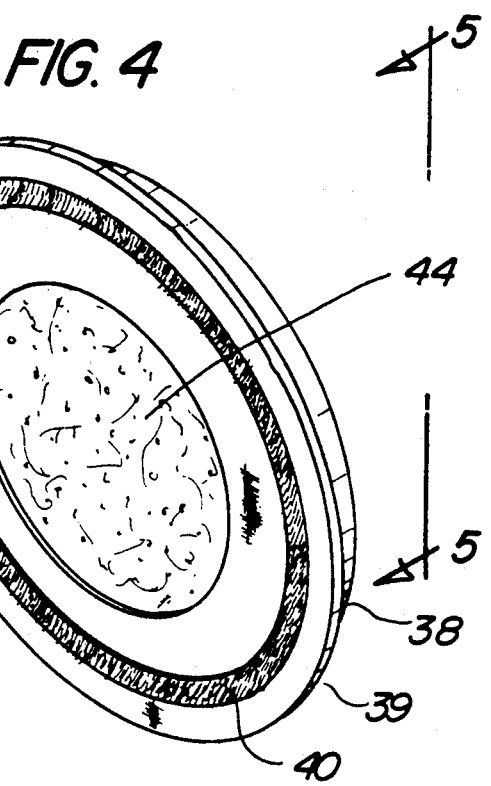
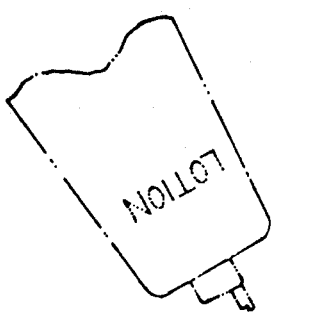
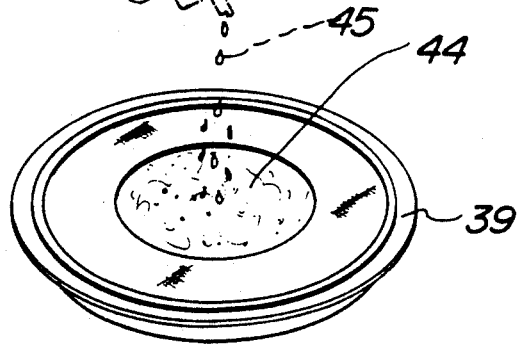
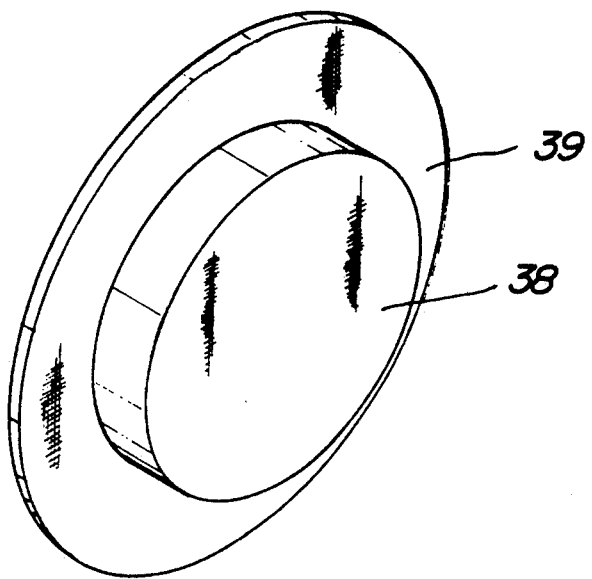

HEATED BRA ARRANGEMENT

BACKGROUND OF THE INVENTION

1. Field of the Invention

The field of invention relates to wearing apparel, and more particularly pertains to a new and improved heated bra arrangement wherein the same is arranged to accommodate pressure relief for lactating individuals.

2. Description of the Prior Art

The use of breast feeding is a more economical and efficient as well as nutritious manner of feeding an infant. Associated with such breast feeding, is typical discomfort due to engorgement and wherein to provide for relief, individuals have typically utilized heated towels and the like directed onto the breast to relieve such stress. The instant invention attempts to overcome deficiencies of the prior art by providing for a readily secured bra structure arranged to direct heat onto a nursing mother's breast to relieve engorgement stress.

Prior art devices directed to nursing bras have heretofore failed to provide such structure and are exemplified in the U.S. Pat. Nos. 4,878,879; 4,911,677; 4,633,876; 4,355,641; and 3,513,852.

Accordingly, it may be appreciated that there continues to be a need for a new and improved heated bra arrangement as set forth by the instant invention addressing both the problems of ease of use as well as effectiveness in construction and in this respect, the present invention substantially fulfills this need.

SUMMARY OF THE INVENTION

In view of the foregoing disadvantages inherent in the known types of bra apparatus now present in the prior art, the present invention provides a heated bra arrangement oriented to direct heat onto a nursing woman's breast. As such, the general purpose of the present invention, which will be described subsequently in greater detail, is to provide a new and improved heated bra arrangement which has all the advantages of the prior art bra apparatus and none of the disadvantages.

To attain this, the present invention provides a heated bra arranged to relieve engorgement in a lactating mother, wherein the bra structure includes a heated wire member directed coextensively in surrounding relationship relative to each cup member in electrical communication with an electrical energy source. The bra structure is further arranged to include a fluid impermeable chamber to accommodate heated water and other fluids to assist in relieving pressure to an individual.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved heated bra arrangement which has all the advantages of the prior art bra apparatus and none of the disadvantages.

It is another object of the present invention to provide a new and improved heated bra arrangement which may be easily and efficiently manufactured and marketed.

It is a further object of the present invention to provide a new and improved heated bra arrangement which is of a durable and reliable construction.

An even further object of the present invention is to provide a new and improved heated bra arrangement which is susceptible of a low cost of manufacture with regard to both materials and labor, and which accordingly is then susceptible of low prices of sale to the consuming public, thereby making such heated bra arrangement economically available to the buying public.

Still yet another object of the present invention is to provide a new and improved heated bra arrangement which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1a is an orthographic view, taken along the lines 1a—1a of FIG. 1 in the direction indicated by the arrows.

FIG. 4 is an isometric illustration of a lotion cup structure utilized by the invention.

FIG. 5 is an orthographic view, taken along the lines 5—5 of FIG. 4 in the direction indicated by the arrows.

FIG. 6 is an isometric illustration of the lotion cup structure accommodating a fluid lotion.

DESCRIPTION OF THE PREFERRED EMBODIMENT

Figure 1:
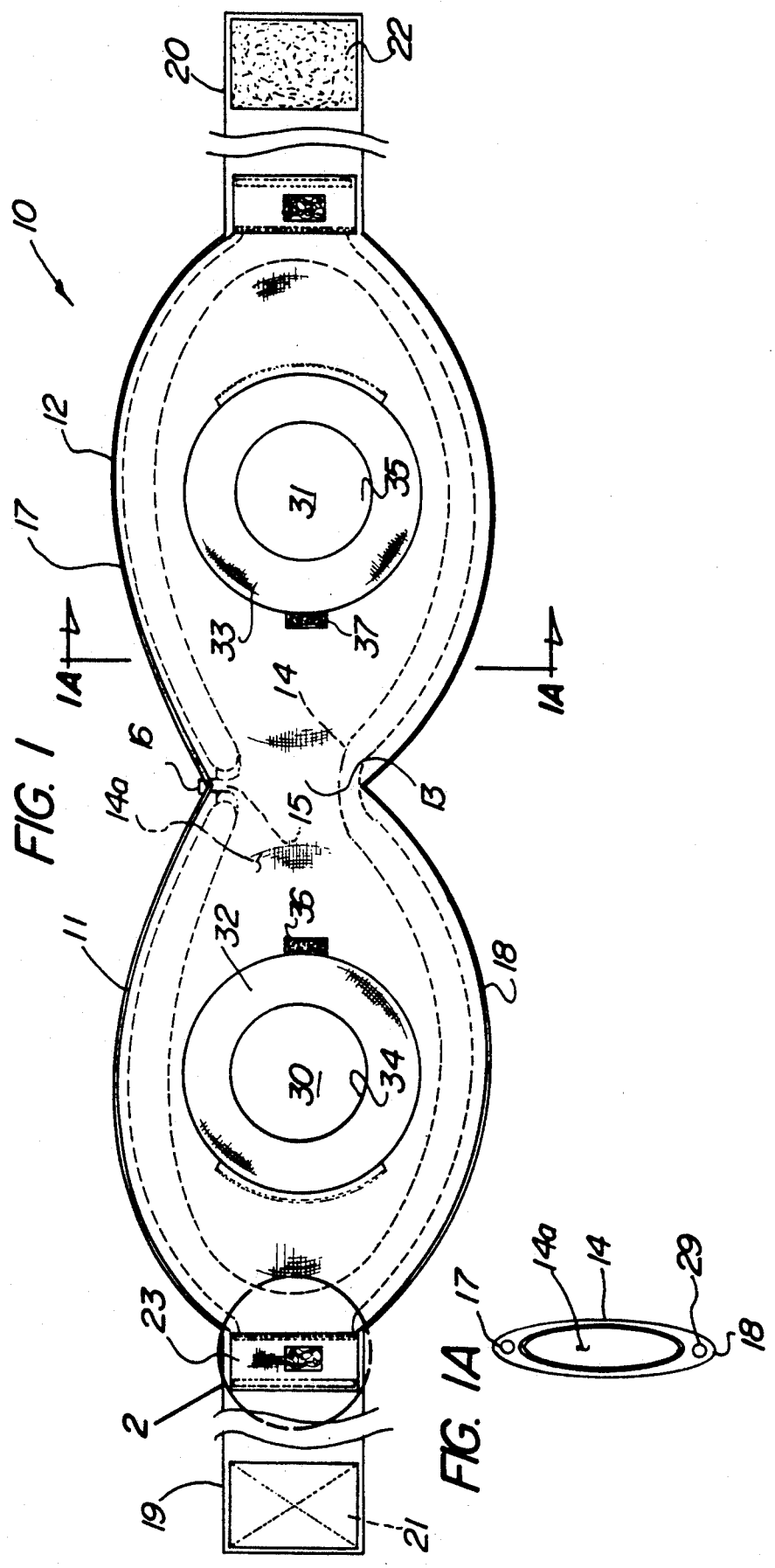
FIG. 1 is an orthographic view of the instant invention.
Figure 2:
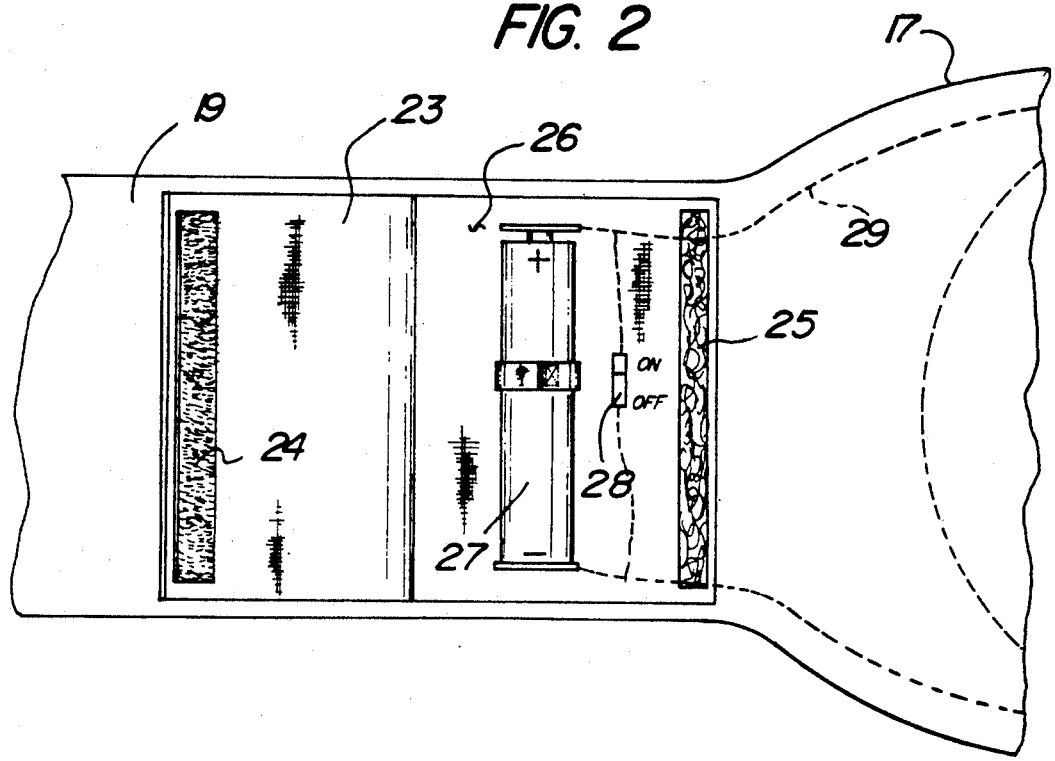
FIG. 2 is an orthographic view of section 2, as set forth in FIG. 1.
Figure 3:
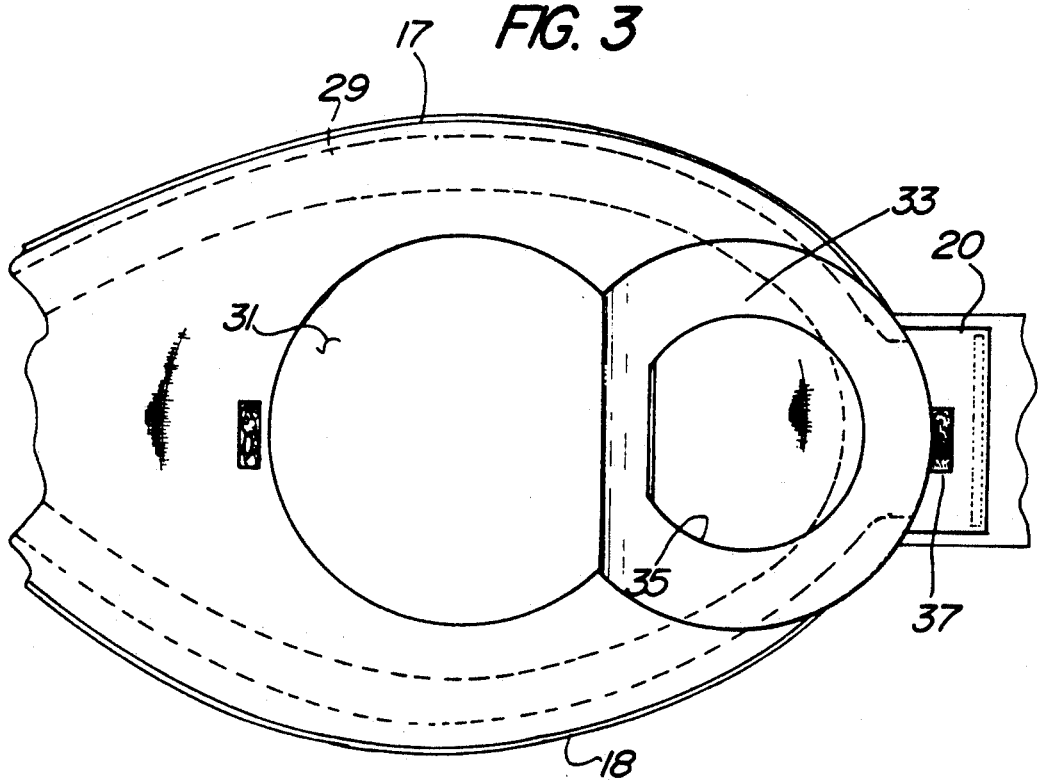
FIG. 3 is an orthographic view of a cup opening flap mounted to an associated cup opening.
Figure 7:
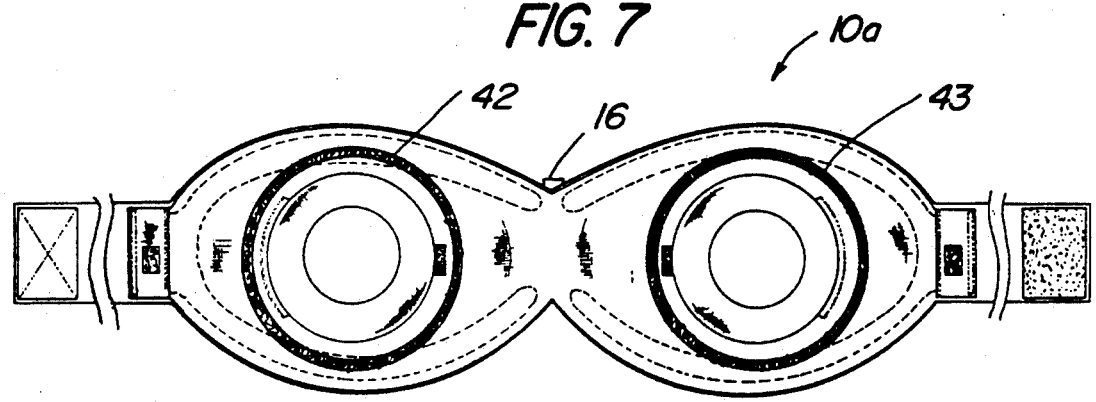
FIG. 7 is an orthographic view of the bra arrangement configured for mounting of the lotion cup structure.
Figure 8:
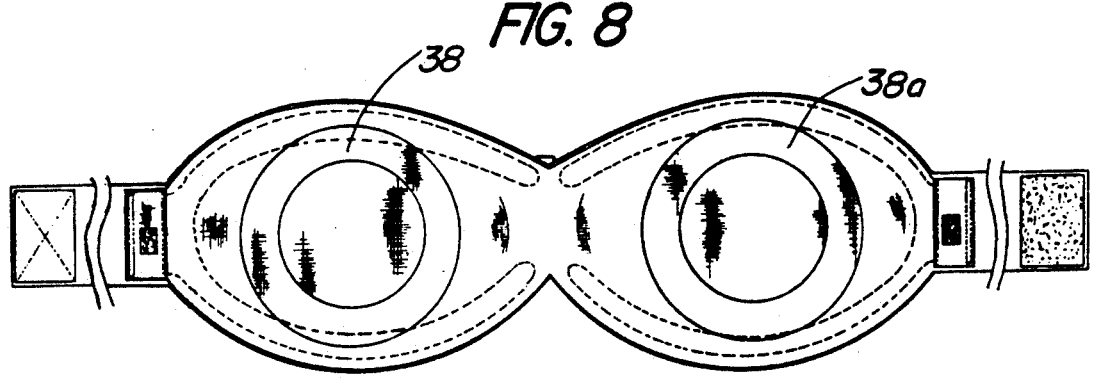
FIG. 8 is an orthographic view of the bra structure receiving the lotion cup members thereon.

With reference now to the drawings, and in particular to FIGS. 1 to 8 thereof, a new and improved heated bra arrangement embodying the principles and concepts of the present invention and generally designated by the reference numeral 10 will be described.

More specifically, the heated bra arrangement 10 of the instant invention essentially comprises a first flexible cup member 11 hingedly mounted to a second flexible cup member 12 by a hinge portion 13 to longitudinally align the first and second cup members 11 and 12 together, as illustrated in FIG. 1. A fluid impermeable bladder 14 is coextensively directed through the first and second flexible cup members 11 and 12 and to the hinge portion 13 having a fill conduit 15 permitting directing of a heated fluid into the fluid chamber 14a of the bladder 14. A fill conduit cap 16 is arranged for securement to an upper distal end of the fill conduit 15 exteriorly of the hinge portion 13 to a continuous upper edge 17 of the bra structure. A lower continuous edge 18 is defined at a lower end of the first and second cup members 11 and 12. A first bra strap 19 and a second bra strap 20 are longitudinally aligned relative to one another and secured to the respective first and second cup members 11 and 12 at opposed ends of the bra structure. The first and second webs 19 and 20 include respective first and second fastener patches 21 and 22 to permit the selective securement of the bra structure about an individual. A battery compartment door flap 23 is mounted onto the first bra strap web 19 to overlie a battery chamber 26. A door flap hook and loop fastener strip 24 is cooperative with a strap hook and loop fastener strip 25. Within the battery chamber 26 is a battery member 27 in electrical communication with an on/off switch 28 into an electrical resistance heating coil 29 that is continuous and directed in surrounding relationship about the bladder 14 within each of the first and second cup members 11 and 12. In this manner, heating of the heating coil 29 is effected to provide for heating the cup members 12. If desired, in lieu of the battery member 27, an alternating current supply may be directed to the resistance heating coil as an alternative utilizing conventional rectifier circuitry or may be utilized alone in lieu of the battery member structure 27.

The first and second cup members 11 and 12 are formed with respective first and second cup openings 30 and 31 having first and second cup opening flaps 32 and 33 pivotally mounted to overlie each of the respective first and second cup openings 30 and 31. The first cup opening flap 32 and the second cup opening flap 33 are formed with respective first and second door openings 34 and 35 to provide for various opening diameter as the first and second door openings 34 and 35 are of a lesser diameter than the first and second cup openings 30 and 31. Securement of the first and second door flaps 32 and 33 is effected by the use of first and second door hook and loop fastener strips 36 and 37 mounted to the respective first and second door flaps 32 and 33 arranged for securement to cooperating fastener structure mounted to the first and second cup members 11 and 12, or alternatively securable to the fabric of the exterior surface of the first and second cup members 11 and 12.

The FIGS. 4-8 illustrate the use of optional lotion cups to include a respective first and second lotion cup 38 and 38a for securement to the first and second cup members 11 and 12 arranged in covering and surrounding relationship relative to the first and second cup openings 30 and 31. Each lotion cup includes a cup flange 39 having an annular hook and loop fastener 40 cooperative with respective first and second bra cup annular hook and loop fastener strips 42 and 43 (see FIG. 7). In this manner, each lotion cup includes a cup sponge member 44 contained therewithin to receive a fluid lotion to enhance comfort and soothing of a nursing mother's breast during the heating procedure.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A heated bra arrangement, comprising,
   a first flexible cup member mounted to a second flexible cup member, with the first flexible cup member and the second flexible cup member longitudinally aligned by an interconnecting hinge portion, and
   a first bra strap web mounted to the first cup member, and a second bra strap web mounted to the second cup member, and
   a continuous upper edge directed along an upper distal end of the first cup member and the second cup member, and
   a continuous lower edge directed along a lower distal edge of the first cup member and the second cup member, and
   a continuous electrical resistance heating coil directed coextensively through the first cup member and the second cup member adjacent the upper edge and the lower edge, and
   the first bra strap web including a battery chamber, the battery chamber including an on/off switch and a battery member contained therewithin, with the battery member and the on/off switch in electrical communication with the electrical resistance heating coil for effecting selective heating of the electrical resistance heating coil, and the first cup member and the second cup member include a respective first cup opening and a second cup opening medially of the respective first cup member and the second cup member, and a fluid impermeable bladder directed coextensively through the first cup member and the second cup member positioned between the electrical resistance heating coil and the first cup opening and the second cup opening, and a bladder fill conduit directed from the bladder to the continuous upper edge, and a fill conduit cap arranged for selective securement to the bladder fill conduit to permit selective filling of the bladder with a heated fluid, and the first cup opening includes a first cup opening flap and the second cup opening includes a second cup opening flap, wherein the first cup opening flap includes a first door opening and the second cup opening flap includes a second door opening directed medially of the respective first cup opening flap and the second cup opening flap, and the first cup opening flap including a first door hook and loop fastener patch, with the second cup opening flap including a second door hook and loop fastener patch for selective securement to the respective first cup member and the second cup member, wherein the first door opening and the second door opening are of a predetermined diameter, and the first cup opening and the second cup opening are of a further predetermined diameter greater than the predetermined diameter, and the battery chamber includes a battery compartment door flap hingedly mounted to the first bra strap web, with the battery compartment door flap including a door flap hook and loop fastener strip, and the first bra strap web including a strap hook and loop fastener strip arranged for selective securement to the door flap hook and loop fastener strip, and a first annular hook and loop fastener strip is mounted to the first cup member in surrounding relationship relative to the first cup opening, and a second annular hook and loop fastener strip is mounted to the second cup member in surrounding relationship relative to the second cup opening, and including a first lotion cup and a second lotion cup, the first lotion cup and the second lotion cup each include a cup flange, wherein the first lotion cup includes a first cup annular hook and loop fastener securable to the first annular hook and loop fastener strip and the second lotion cup includes a second cup annular hook and loop fastener for securement to the second annular hook and loop fastener strip, the first lotion cup and the second lotion cup include a cup sponge member, the cup sponge member of the first lotion cup and the second lotion cup arranged for receiving fluid lotion therewithin.

* * * * *